(12) United States Patent
Siddiqui et al.

(10) Patent No.: US 6,511,675 B2
(45) Date of Patent: Jan. 28, 2003

(54) COMPOSITION AND METHOD FOR CORRECTING A DIETARY PHYTOCHEMICAL DEFICIENCY

(75) Inventors: Idrees Siddiqui, Richmond, VA (US); David Groh, Temecula, CA (US); Robin Dykhouse, Newport Beach, CA (US); Audra Davies, Long Beach, CA (US); Carl S. Rehnborg, Laguna Beach, CA (US); Kerry Stonebrook, Pomona, CA (US)

(73) Assignee: Access Business Group International, LLC, Ada, MI (US)

( * ) Notice: Subject to any disclaimer, the term of this patent is extended or adjusted under 35 U.S.C. 154(b) by 29 days.

(21) Appl. No.: 09/878,377

(22) Filed: Jun. 12, 2001

(65) Prior Publication Data

US 2002/0025350 A1 Feb. 28, 2002

Related U.S. Application Data

(60) Provisional application No. 60/210,746, filed on Jun. 12, 2000.
(51) Int. Cl.[7] .............................................. A61K 47/00
(52) U.S. Cl. ...................... 424/439; 424/400; 424/489; 424/725
(58) Field of Search ................................ 424/400, 439, 424/489, 725

(56) References Cited

U.S. PATENT DOCUMENTS

| | | |
|---|---|---|
| 5,356,636 A | 10/1994 | Schneider et al. |
| 5,401,502 A | 3/1995 | Wunderlich et al. |
| 5,514,382 A | 5/1996 | Sultenfuss |
| 5,578,336 A | 11/1996 | Monte |
| 5,612,039 A | 3/1997 | Policappelli et al. |
| 5,654,011 A | 8/1997 | Jackson et al. |
| 5,686,108 A | 11/1997 | Pusateri et al. |
| 5,770,217 A | 6/1998 | Kutilek, III et al. |
| 5,807,586 A | 9/1998 | Jackson et al. |
| 5,830,887 A | 11/1998 | Kelly |
| 5,840,278 A | 11/1998 | Coleman |
| 5,882,646 A | 3/1999 | Pusateri et al. |
| 5,904,924 A | 5/1999 | Gaynor et al. |
| 5,948,443 A | 9/1999 | Riley et al. |
| 5,955,102 A | 9/1999 | Gorenbein et al. |
| 5,972,985 A | 10/1999 | Thomas et al. |
| 5,976,548 A | 11/1999 | Hsia et al. |
| 5,976,568 A | 11/1999 | Riley |
| 5,985,338 A | 11/1999 | Suh et al. |

Primary Examiner—Thurman K. Page
Assistant Examiner—Charesse Evans
(74) Attorney, Agent, or Firm—Finnegan, Henderson, Farabow, Garrett & Dunner LLP

(57) ABSTRACT

The invention is directed to a composition and method for correcting a dietary phytochemical deficiency, wherein the phytochemicals include sulphoraphane, naringen, hesperidin, narirutin, quercetin, β-carotene, lutein, lycopene, and isoflavones. The composition may also comprise additional vitamins and minerals.

18 Claims, No Drawings

COMPOSITION AND METHOD FOR CORRECTING A DIETARY PHYTOCHEMICAL DEFICIENCY

This application claims priority of U.S. Provisional Application No. 60/210,746, filed June 12, 2000.

FIELD OF THE INVENTION

The present invention relates to a composition and method for correcting a dietary inadequacy, including a diet-induced inadequacy, of phytochemicals, vitamins, and minerals.

BACKGROUND OF THE INVENTION

Dietary supplements are often used for the treatment and prevention of various disorders. Such supplements are often targeted for specific diseases. For example, U.S. Pat. No. 5,976,568 is directed to a modular system of dietary supplement compositions for the treatment and prevention of, among other things, coronary heart disease. The modular system comprises several different modules, or formulas, each of which is a different combination of vitamins and minerals such as antioxidants and folic acid.

Similarly, U.S. Pat. No. 5,830,887 relates to compositions enriched with natural phytoestrogens selected from genistein, daidzein, formononetin, and biochanin A. The compositions are disclosed to be useful for promoting health in cases of cancer, pre-menstrual syndrome, menopause, or hypercholesterolemia.

U.S. Pat. No. 5,882,646 relates to a brassica vegetable supplement having high levels of sulforaphane and low levels of sulforaphane-nitrile. Brassica vegetables include, for example, broccoli, cabbage, kale, and cauliflower. The brassica vegetable supplements allow consumers who don't like the taste of brassica vegetables to nevertheless reap the dietary benefits therefrom.

U.S. Pat. No. 5,770,217 is directed to a dietary supplement comprising herbs and herbal extracts, vitamins, minerals, and amino acids effective in modulating hematological toxicities, enhancing the immune system, and maintaining appetite and weight.

A large portion of the population does not practice desirable eating habits, namely an adequate intake in quantity and variety of food to meet the U.S. Recommended Dietary Allowances. Only 22% of the subjects of a National Cancer Institute Study consumed the recommended daily number of dietary servings of fruits and vegetables. This is in spite of the fact that the recommended dietary intake of fruits and vegetables is well-known. For example, *The California Daily Food Guide: Dietary Guidelines for Californians*, California Department of Health Services (1990) recommends that each person consume at least five to nine servings of fruit and vegetables per day, including one serving of a vitamin A-rich deep green or dark orange fruit or vegetable, and at least one serving of a vitamin C-rich fruit or vegetable. Additionally, each person should consume at least 3 servings per week of vegetable protein in the form of legumes, nuts, or seeds. Some researchers suggest that a target of 400 grams (13 ounces) of fruits and vegetables is a sensible goal for the optimal quantity to be consumed daily. In terms of variety, persons should eat at least three different colors of fruits and vegetables daily.

Lifestyle factors such as smoking, levels of physical activity, exposure to toxic environmental compounds, dieting, use of certain medications such as oral contraceptives, the use of certain food additives such as OLESTRA, and the avoidance of certain foods (for example, due to lactose intolerance, which occurs in over 25% of the population), can also contribute to low or deficient intakes of nutrients.

Although researchers haven't yet ascertained the optimal plant-based diet, it's clearly one that is rich in fruits and vegetables. It is believed that the optimal diet comprises, in large part, the following nine plant foods (and phytochemicals).

Red, yellow, and orange fruits, which are rich in, for example, carotenoids, flavonoids, and coumarins;

Red, yellow, and orange vegetables, which are rich in carotenoids, flavonoids, and capsaicin;

Cruciferous and leafy green vegetables, which are rich in indoles, carotenoids, and isothiocyanates;

Soy and soy products which are rich in flavonoids, phytosterols, saponins, and protease inhibitors;

Garlic, which is rich in allyl sulfides and quercetin;

Beans and other legumes, which are rich in phytosterols, isoflavones, protease inhibitors, and saponins;

Whole grains, which are rich in lignans, phenolic acids, and phytosterols;

Nuts and seeds, which are rich in lignans; and

Tea (green or black), which is rich in the catechin flavonoids.

It is difficult, if not impossible, to make diet recommendations on the precise quantity of each plant or its constituents that prevent diseases or alter disease progression. Nevertheless, leading health authorities offer dietary guidelines for general health promotion and disease risk reduction.

Research has shown that the typical U.S. diet is lacking in phytochemicals. Phytochemicals generally refer to plant-derived compounds which, when taken daily in combination with vitamins and minerals, provide improved cardiovascular and bone health, an improved antioxidant profile, decreased free radical damage, and overall enhancement of the body's natural defense system. The difference between the recommended amount of phytochemicals and the amount ingested in a typical diet is referred to as, for the purposes of the present invention, a gap. The following table represents a gap analysis for various phytochemicals.

| Phytochemical | Recom. Level | Typical U.S. Diet | Gap |
| --- | --- | --- | --- |
| Total Carotenoids | 9–18 mg/day | 6.0 mg/day | 3–12 mg/day |
| β-carotene | 3–13 mg | 2.6 mg | 0.4–10.4 mg/day |
| Lutein | 19.5–25.6 mg | 1.8 mg | 20.75 mg |
| Lycopene | 4.2–10 mg | 2.2 mg | 2–7.8 mg |
| Total Flavonoids | 0–1500 mg/day | 1000 mg/day | 100 mg/day |
| Isothiocyanates | 19–38 mg/day | 0 mg | 19 mg |
| Isoflavones | 48–60 mg/day | 0.1–20.3 mg/day | 33.7–53.9 mg/day |

The existence of this gap has significant health implications, as the link between ingestion of phytochemicals and a decreased incidence of several chronic degenerative diseases, such as cancer and cardiovascular disease, has been demonstrated. For example, in a case-cohort study of 8006 Hawaiian men of Japanese ancestry, the association between diet and the risk of gastric cancer was investigated. Dietary data obtained from 111 men with stomach cancer and 361 cancer-free men were analyzed for intake of selected foods, food groups, and nutrients. The researchers reported that the consumption of all types of vegetables exhibited a statistically significant inverse trend with gastric cancer risk. Green and cruciferous vegetables exhibited a similar but weaker protective effect. Chyou, P. H. et al., "A Case-Cohort Study of Diet and Cancer," *Cancer Res.* 50:7501–4 (1990).

In a prospective cohort study of 41,837 postmenopausal women, the association of fruit and vegetable consumption with lung cancer risk was investigated. The researchers found that the risk of lung cancer was approximately halved when the consumption of fruits and vegetables increased from 24 or less servings to an excess of 48 servings per week. Similarly, the risk of lung cancer was approximately halved when the consumption of green leafy vegetables, including spinach and parsley sources, increased from 1 or fewer servings to six or more servings per week. Steinmetz, K. et al., "Vegetables, Fruit, and Lung Cancer in the Iowa Women's Health Study," *Cancer Res.* 53:536–43 (1993).

Another study found that an increased intake of fresh tomatoes (a major source of lycopene) was associated with a pattern of protection for all sites of digestive tract cancer. Stahl, W. et al., "Lycopene: A Biologically Important Carotenoid for Humans?" *Arc. Biochem. Biophys.* 336:1–9 (1996).

A case-controlled study of approximately 13,000 women aged 65–74 years diagnosed with invasive breast cancer found that eating raw or cooked carrots and spinach more than twice weekly reduced the risk of breast cancer by 44%, compared with no intake. Longnecker, M. P. et al., "Intake of Carrots, Spinach, and Supplements Containing Vitamin A in Relation to Risk of Breast Cancer," *Cancer Epid. Biomarkers Prev.* 6:887–92 (1997).

As previously indicated, the typical westernized diet, specifically the North American diet, is significantly lacking in beneficial phytochemicals, typically found in many fruits and vegetables, due to inadequate consumption and imbalanced dietary intake. Not only is the westernized diet characterized by phytochemical deficiencies but typically vitamin and mineral intakes are also compromised as a result of inadequate consumption and imbalanced dietary intakes. There exists a need to correct dietary deficiencies of phytochemicals, vitamins, and minerals.

SUMMARY OF THE INVENTION

The present invention provides a means with which a unique combination of phytochemicals, vitamins, minerals and specialty ingredients can reduce or eliminate the dietary gap that exists between an optimal diet and a westernized diet. This combination, particularly when combined with essential vitamins and minerals, provides substantial health benefits. The present invention provides phytochemicals, vitamins and minerals that have been shown to support the health of people who consume a nutritionally and phytochemically deficient diet; replenish serum nutrient and phytochemical levels as a result of inadequate diets to levels associated with decreased risk of certain degenerative disease states; improve antioxidant and nutrient status; minimize free radical damage that typically occurs as a result of normal aging processes and exposure to environmental stresses; and improve the status of specific biomarkers indicative of optimal health, namely homocysteine, lipid oxidation byproducts, vitamin and mineral status, antioxidant measures, and glutathione peroxidase. β-carotene, α-lipoic acid, selenium, and vitamins C and E improve the antioxidant profile of a person. Increased levels of folic acid and vitamins E, $B_6$, and $B_{12}$ target and improve cardiovascular health. Calcium, magnesium, and vitamin D targets and improves bone health. Increased B vitamins improve energy metabolism. The compositions according to the invention provide a range of 2% to 2500% of the U.S. Recommended Daily Intake of over 24 vitamins and minerals. The compositions furthermore significantly bridge the gap in phytochemical intake by providing 11 plant concentrates to deliver a wide range of phytochemicals.

To achieve these and other advantages, and in accordance with the purpose of the invention as embodied and broadly described herein, the present invention is drawn to a dietary supplement composition containing, but not limited to, the following phytochemicals: sulphoraphane, naringen, hesperidin, narirutin, quercetin, β-carotene, lutein, lycopene, and isoflavones.

According to another aspect of the present invention, there is provided a method for correcting an inadequacy of phytochemicals by administering a dietary supplement to a subject known to have a phytochemical deficiency, such as a diet-induced phytochemical deficiency, wherein the supplement contains vitamins, minerals, and at least the following nine phytochemicals: sulphoraphane, naringen, hesperidin, narirutin, quercetin, β-carotene, lutein, lycopene, and isoflavones.

The present invention is further drawn to a method for improving the antioxidant profile of the human body through the administration of a dietary supplement containing an effective amount of vitamins C and E, α-lipoic acid, selenium and phytochemicals comprising sulphoraphane, naringen, hesperidin, narirutin, quercetin, beta-carotene, lutein, lycopene, and isoflavones to a subject in need of an improved antioxidant profile.

Another aspect of the present invention is a method for targeting and improving cardiovascular and bone health through the administration of a dietary supplement containing an effective amount of calcium, magnesium, folic acid, vitamins $B_6$, $B_{12}$, C, and E, and phytochemicals comprising sulphoraphane, naringen, hesperidin, narirutin, quercetin, β-carotene, lutein, lycopene, and isoflavones to a subject in need of improved cardiovascular and bone health.

A further embodiment of the present invention is a method for decreasing free radical damage in the human body through the administration of a dietary supplement containing an effective amount of vitamin C, zinc, and phytochemicals comprising sulphoraphane, naringen, hesperidin, narirutin, quercetin, β-carotene, lutein, lycopene, and isoflavones to a subject in need thereof.

Yet another aspect of the present invention is a method for enhancing the natural defense system of the human body through the administration of a dietary supplement containing an effective amount of vitamins C and E, α-lipoic acid, selenium and phytochemicals comprising sulphoraphane, naringen, hesperidin, narirutin, quercetin, β-carotene, lutein, lycopene, and isoflavones to a subject.

Additional objects and advantages of the invention will be set forth in part in the description which follows, and in part will be apparent from the description, or may be learned by practice of the invention. It is to be understood that both the foregoing general description and the following detailed description are exemplary and explanatory only and are not restrictive of the invention as claimed.

DETAILED DESCRIPTION OF THE INVENTION

Reference will now be made in detail to certain exemplary embodiments of the present invention. The invention relates to a dietary supplement composition comprising at least the following nine phytochemicals: sulphoraphane, naringen, hesperidin, narirutin, quercetin, β-carotene, lutein, lycopene, and isoflavones. Further, the invention relates to a method for correcting a diet-induced deficiency of phytochemicals by administering a dietary supplement to a subject known to have a phytochemical deficiency, such as a diet-induced phytochemical deficiency, wherein the supplement contains vitamins, minerals and at least the following nine phytochemicals: sulphoraphane, naringen, hesperidin, narirutin, quercetin, β-carotene, lutein, lycopene, and isoflavones.

The nine phytochemicals present in the inventive composition may be obtained from a minimum of 16 plant sources which include the following combination of plant materials: alfalfa, watercress, parsley, Fava d'Anta, tomato, broccoli, horseradish, grapefruit, mandarin, lemon, Spirulina, algae, carrot, palm, tomato, marigold and acerola.

The dietary supplement of the present invention contains vitamins, minerals, and specialty ingredients known to improve the body's natural defenses against oxidants, free radicals, heart disease, and to provide enhanced metabolism.

Suitable vitamins for use in the compositions and methods of the present invention include, for example, vitamin A, vitamin C, vitamin D, vitamin E, vitamin K, vitamin $B_6$, vitamin $B_{12}$, thiamin, riboflavin, niacin, folic acid, biotin, and pantothenic acid.

Suitable minerals for use in the compositions and methods of the present invention include, for example, calcium, magnesium, iodine, potassium, copper, zinc, phosphorus, manganese, chromium, selenium, molybdenum, vanadium, and boron. Other vitamins and minerals may also be used.

Additional ingredients which may be included in the compositions of the invention are, for example, MSM and α-lipoic acid.

According to one aspect of the invention, the phytochemicals are administered to a person without additional dietary supplements such as vitamins, minerals, and specialty ingredients.

According to another aspect of the present invention, the phytochemicals are administered to a person in need thereof either simultaneously or sequentially with other nutrients such as, for example, vitamins, minerals, and specialty ingredients.

The following tables illustrate representative daily amounts of suitable phytochemicals, vitamins, minerals, and specialty ingredients which may be included in the compositions of the invention. Tables 1–3 illustrate one embodiment of the invention, which may be designated as Formula 1; Table 4 provides two additional embodiments of the invention, designated as Formulae 2 and 3. These embodiments are exemplary only, and the dosages may be altered without departing from the spirit and scope of the invention.

TABLE 1

11 Concentrates providing 9 Phytochemicals

| Concentrate/Phytochemical | Amounts/Day |
|---|---|
| Brassica Concentrate, mg | 100 |
| Sulphoraphane, mg | 0.05 |
| Citrus Bioflavonoids Concentrate, mg | 150 |
| Naringen, mg | 4.5 |
| Hesperidin, mg | 9 |
| Narirutin, mg | 0.75 |
| Quercetin, mg | 100 |
| Natural β-Carotene, mg | 100 |
| β-Carotene, IU | 7500 |
| Lutein 5% Concentrate, mg | 20 |
| Lutein, mg | 1 |
| Lycopene 5% Concentrate, mg | 20 |
| Lycopene, mg | 1 |
| Soy Isoflavone Concentrate, mg | 25 |
| Isoflavones, mg | 10 |
| Spirulina Concentrate, mg | 50 |
| NUTRILITE Acerola Cherry Conc., mg | 400 |
| NUTRILITE Alfalfa Conc., mg | 150 |
| NUTRILITE AWP XX Conc., mg | 323 |

NUTRILITE acerola cherry concentrate and NUTRILITE alfalfa concentrate are both available from Amway Corp., (Ada, Mich.). NUTRILITE AWP XX concentrate (which contains alfalfa/watercress/parsley) is also available from Amway.

TABLE 2

Vitamins

| Vitamin | Amount/Day | % Daily Value |
|---|---|---|
| Vitamin A (75% as β-Carotene), IU | 10000 | 200% |
| Vitamin C, mg | 500 | 833% |
| Vitamin D, IU | 400 | 100% |
| Vitamin E, IU | 300 | 1000% |
| Vitamin K, mcg | 80 | 100% |
| Thiamin, mg | 25 | 1667% |
| Riboflavin, mg | 25 | 1471% |
| Niacin, mg | 70 | 350% |
| Vitamin $B_6$, mg | 50 | 2500% |
| Vitamin $B_{12}$, mcg | 100 | 1667% |
| Folic Acid, mcg | 800 | 100% |
| Biotin, mcg | 300 | 100% |
| Pantothenic Acid, mg | 50 | 500% |

TABLE 3

Minerals

| Vitamin | Amount/Day | % Daily Value |
|---|---|---|
| Calcium, mg | 1000 | 100% |
| Magnesium, mg | 500 | 125% |
| Iodine, mcg | 150 | 100% |
| Potassium, mg | 80 | |
| Copper, mg | 2 | 100% |
| Zinc, mg | 20 | 133% |
| Phosphorus, mg | 20 | 2% |
| Manganese, mg | 5 | 250% |
| Chromium, mcg | 120 | 100% |
| Selenium, mcg | 100 | 143% |
| Molybdenum, mcg | 75 | 100% |
| Vanadium, mcg | 20 | |
| Boron, mg | 1 | |

TABLE 4

| | Formula 2 | Formula 3 |
|---|---|---|
| Vitamin A, IU (Beta carotene) | 10,000 | 3000 |
| Vitamin $B_1$, mg | 25 | 1.65 |
| Vitamin $B_2$, mg | 25 | 1.8 |
| Vitamin $B_6$, mg | 50 | 2.4 |
| Niacin, mg | 70 | 25.5 |

TABLE 4-continued

| | Formula 2 | Formula 3 |
|---|---|---|
| Folic Acid, mcg | 800 | 300 |
| Vitamin $B_{12}$, mcg | 100 | 3.6 |
| Pantothenic Acid, mg | 50 | 7.5 |
| Biotin, mcg | 300 | 45 |
| Vitamin C, mg | 500 | 150 |
| Vitamin D, IU | 400 | 150 |
| Vitamin E, IU | 300 | 22.4 |
| Vitamin K, mg | 80 | 0 |
| Calcium, mg | 900 | 700 |
| Magnesium, mg | 450 | 310 |
| Iron, mg | 0 | 10 |
| Copper, mg | 2 | 1.8 |
| Iodine, mcg | 150 | 150 |
| Zinc, mg | 20 | 11 |
| Chromium, mcg | 120 | 35 |
| Selenium, mcg | 100 | 60 |
| Molybdenum, mcg | 75 | 30 |
| Lutein, mg | 1 | 1 |
| Lycopene, mg | 1 | 1 |
| Quercetin, mg | 100 | 100 |
| Brassica Concentrate | 100 | 25 |
| AWP, mg | 323 | 1035 |
| Acerola Concentrate, mg | 300 | 975 |
| Citrus Bioflavanoids, mg | 150 | 100 |
| Grape Seed extract, mg | 0 | 50 |
| Spinach, mg | 0 | 68.5 |
| Broccoli Sprout Extract, mg | 0 | 35 |
| Alfalfa Concentrate | 0 | 100 |
| Carrot | 0 | 34.3 |
| Green tea extract, mg | 0 | 25 |

According to one aspect of the invention, the supplement according to the present invention is administered as three separate tablets, all three of which are administered twice a day. However, the selection of other administration forms and unit dosages is within the skill of the ordinary practitioner.

The dietary supplements of the present invention may be formulated using any food and pharmaceutically acceptable forms of the phytochemicals, vitamins, minerals, and other nutrients, including their salts. They may be formulated into tablets, powders, gels, or liquids (a tablet, for the purposes of the present invention and as used throughout the application disclosure, refers to any form of a solid oral dosage, including but not limited to tablets, caplets, capsules, powders, etc.). The dietary supplements may be formulated as powders, for example, for mixing with consumable liquids such as milk, juice, water, or consumable gels or syrups for mixing into other dietary liquids or foods. The dietary supplements of this invention may also be formulated with other foods or liquids to provide pre-measured supplemental foods, such as single-serving bars, for example. Flavorings, binders, protein, complex carbohydrates, and the like may be added as needed.

According to one aspect of the invention, when the dietary supplements are provided in the form of tablets, the three tablets that constitute each of the daily doses may contain one or more of the following ingredients: calcium, spirulina, β-carotene (BC), pyridoxine HCl (vitamin A), pantothenic acid, folic acid, magnesium, α-lipoic acid, vitamin $B_2$, vitamin $B_1$, vitamin $B_{12}$, vitamin $B_6$, iodide, vitamin D, citrus bioflavonoid concentrates, lycopene, niacin, niacinamide, quercetin, brassica, MSM, lutein, vitamin E, mixed tocopherols, and acerola concentrate.

The first tablet, which provides, inter alia, essential vitamins, contains, in addition to the above-identified concentrate, ascorbic acid (vitamin C), calcium carbonate, magnesium oxide, biotin, boron aspartate, and vanadyl sulfate.

The second tablet, which provides, interalia, essential minerals, contains, in addition to the above-identified concentrate, magnesium oxide, zinc gluconate, manganese gluconate, copper gluconate, chromium chloride, sodium selenite, and sodium molybdate.

The third tablet, which provides, inter alia, phytochemicals, contains, in addition to the above-identified concentrate, phytonadione.

The invention will be illustrated by, but is not intended to be limited to, the following examples.

EXAMPLE 1

By way of example, three tablets are prepared which provide phytochemicals, vitamins, minerals, and specialty ingredients. The unit "amount/2 tablets/day" provided for certain active ingredients means that the amount recited is given in the number of, e.g., milligrams, provided in a two-tablets per day dosage. The ingredients for which no amounts are given are standard in this art, and the amounts may be varied for purposes well-known to those of ordinary skill in this art.

TABLET 1

| Ingredients | Amount/2 tablets/day |
|---|---|
| Ascorbic Acid, 97% | 440 mg |
| Biotin Trituration, 1% | 0.3 mg |
| Boron Aspartate, 5% | 1.0 mg |
| Calcium Carbonate, Gran., D.C./A. | 168 mg |
| Carob Powder | |
| Cellulose Gum, Modified NF | |
| Magnesium Oxide Heavy DC | 143.85 mg |
| Magnesium Stearate, Vegetable | |
| Microcrystalline Cellulose, Silicified | |
| Silicone Dioxide, NF Fine Powder | |
| Vitamin E, d-α-Tocosuccinate | 92 IU |
| H.P.M.C. 5 cps Aqueous C/S (optional) | |
| CONCENTRATE (See Below) | 626 mg |

TABLET 2

| Ingredients | Amount/2 tablets/day |
|---|---|
| Calcium Carbonate, Gran., D.C/A. | 257 mg |
| Cellulose Gum, Modified NF | |
| Chromium Trituration, 10% | 120 µg |
| Copper Gluconate | 2 mg |
| Calcium | 25.79 mg |
| Dicalcium Phos., Dihyd., Unmilled | 20 mg |
| Magnesium Oxide, Heavy, D.C. | 128 mg |
| Magnesium Stearate, Vegetable | |
| Manganese Gluconate, FCC | 5 mg |
| Microcrystalline Cellulose, Silicified | |
| Molybdenum Trituration, 10% | 75 µg |
| Potassium Chloride | 80 mg |
| Selenium Trituration, 10% | 100 µg |
| Silicone Dioxide, NF Fine Powder | |
| Vitamin E, d-α-Tocosuccinate | 92 IU |
| H.P.M.C. 5 cps Aqueous C/S (optional) | |
| Zinc Gluconate, Gran. | 20 mg |
| CONCENTRATE (See Below) | 626 mg |

TABLET 3

| Ingredients | Amount/2 tablets/day |
| --- | --- |
| Calcium Carbonate, Gran., D.C./A. | 357 mg |
| Cellulose Gum, Modified NF | |
| Magnesium Oxide, Heavy, D.C. | 180 mg |
| Magnesium Stearate, Vegetable | |
| Microcrystalline Cellulose, Silicified | |
| Phytonadione 1%, S.D. | 0.08 mg |
| Silicon Dioxide, NE Fine Powder | |
| Vanadium | 0.020 mg |
| H.P.M.C. 5 cps Aqueous C/S (optional) | |
| Vitamin E d-α-Tocosuccinate | 92 IU |
| CONCENTRATE (See Below) | 626 mg |

In addition to the above ingredients, all three tablets contain a concentrate (Double X Gold Standard concentrate, available from Access Business Group LLC) having ingredients in the following amounts:

CONCENTRATE

| Ingredients | Amount/2 tablets/day |
| --- | --- |
| Calcium | 30.2 mg |
| Spirulina | 16.66 mg |
| β-Carotene (BC) | 2500 IU |
| Vitamin A | 833.33 IU |
| PA | 16.67 mg |
| Folic Acid | 266.67 micrograms |
| Magnesium | 0.13 mg |
| α-Lipoic Acid | 3.333 mg |
| Vitamin $B_2$ | 8.33 mg |
| Vitamin $B_1$ | 8.33 mg |
| Vitamin $B_{12}$ | 33.33 μg |
| Vitamin $B_6$ | 16.67 mg |
| Iodide | 50.11 μg |
| Vitamin D | 133.33 IU |
| Citrus bioflavonoid concentrates | 50 mg |
| Lycopene | 0.33 mg |
| Niacin | 3.33 mg |
| Niacinamide | 20 mg |
| Quercetin | 33.33 mg |
| Brassica | 33.33 mg |
| MSM | 20.0 mg |
| Lutein | 0.33 mg |
| Vitamin E Mixed Tocopherols | 8.33 IU |
| Acerola Concentrate | 20 mg Vitamin C Activity |

The three tablets, when administered twice a day, contribute to filling the gap in phytochemicals that is present in the typical diet.

EXAMPLE 2

Clinical Study

A clinical study was performed to assess the nutritional, phytochemical, and antioxidant status of individuals consuming a typical "western" diet plus the label dose of a composition according to the invention. The hypothesis was that consumption of the label dose of the invention would bridge the phytochemical gap between those consuming a "western" diet and those consuming an "optimal," more plant-based diet.

The "western" and "optimal" diet groups were determined after administration of a food frequency questionnaire and application of the Recommended Foods Score (RFS). The RFS consists of 23 foods, 14 of which are fruits and vegetables, that when consumed on a weekly basis have been associated with reduced mortality. This was demonstrated in a cohort study of 42,254 women. Those with a mean RFS of 16.0 (highest quartile) had an all-cause mortality relative risk of 0.69 compared to those with a mean RFS of 6.4 (lowest quartile). The published results did not provide the number of fruits and vegetables consumed by each group. It was noted that those in the highest quartile consumed significantly more calories (131%), fiber (200%), vitamin C (230%), folate (181%), and provitamin A carotenoids (253%) compared to those in the lowest quartile. In one trial, the "western" diet group had a mean RFS of 5.65 while the "optimal" diet group had a mean RFS of 15.30. In addition, the "western" diet group consumed an average of 3.2 servings of fruits/vegetables per day while those in the "optimal" diet group consumed approximately 7.81 daily servings.

In this parallel, single blind study, 46 healthy adults consumed either a label dose of Double X 2000 or a placebo for six weeks. The outcome measure relevant to the present invention was a serum vitamin/carotenoid/phytochemical profile. Specifically, the study population was tested for plasma levels of α-tocopherol, γ-tocopherol, vitamin $B_{12}$, β-carotene, and folate were tested at baseline and at six weeks.

| Results | | |
| --- | --- | --- |
| | Western + Double X | Optimal + Placebo |
| α-tocopherol | +19 μM | No change |
| γ-tocopherol | −2.8 μM | −1.39 μM |
| vitamin $B_{12}$ | +212 pg/mL | −8 pg/mL |
| β-carotene | +0.22 μM | No change |
| Folate | +11.5 nG/mL | −1.7 nG/mL |

The results show that following six weeks of supplementation, subjects consuming the "western" diet plus Double X 2000 had significantly increased plasma levels of vitamins E (α-tocopherol), $B_{12}$, β-carotene, and folate. In contrast, there were insignificant changes in subjects consuming the "optimal" diet plus placebo.

EXAMPLE 3

Preparatory Example

The following examples relate to methods of preparing the above three tablets. The ingredients are the same as those referred to above for Tablets 1, 2, and 3. The selection of other methods for preparing the tablets and other suitable delivery vehicles are within the skill of the ordinary practitioner.

Tablet 1

Vitamin E d-α-tocosuccinate is passed through a SWECO separator equipped with a 6-mesh screen directly into a P.K. 100 blender. Silicon dioxide (NF fine powder) is passed through a SWECO separator equipped with a 20-mesh screen directly into a P.K. 100 blender. The ingredients are blended for ten minutes. The concentrate (Double X Gold Standard Concentrate) is added. The mixture is blended for a further five minutes. Ascorbic acid (97%), calcium carbonate (90, D.C.), and magnesium oxide (heavy, D.C.) are added.

Next, the following ingredients are passed through a SWECO separator equipped with a 20 mesh screen directly into the P.K. 100 blender: cellulose gum, carob powder, boron aspartate (5%), biotin trituration (1%), and microcrystalline cellulose (silicified). The mixture is blended for an additional 20 minutes.

Magnesium stearate (vegetable) is passed through a SWECO separator equipped with a 20 mesh screen directly into the P.K. 100 blender. The mixture is blended for an additional five minutes. The resulting mixture is discharged into totes or supersacks, compressed, and punched by means known to those of ordinary skill in the art to form the tablets.

Tablet 2

Copper gluconate, chromium trituration (10%), molybdenum trituration (10%), selenium trituration (10%), and manganese gluconate (FCC) are added to a 55 gallon stainless steel drum, and the mixture is blended on a drum tumbler for five minutes. The blended mixture is passed through a Fitzmill equipped with a 0.065" plate, medium speed, knives forward into a polylined drum. Zinc gluconate (gran.) is passed through a Fitzmill equipped with a 0.065" plate, medium speed, knives forward, into a polylined drum.

Vitamin E d-α-tocosuccinate is passed through a SWECO separator equipped with a 6-mesh screen directly into a P.K. 100 blender. Silicon dioxide (NF Fine Powder) is passed through a SWECO separator equipped with a 20 mesh screen directly into the P.K. 100 blender. The vitamin E d-α-tocosuccinate and silicon dioxide are blended for ten minutes.

The concentrate (Double X Gold Standard Concentrate) is passed through a SWECO separator equipped with a 6-mesh screen into the P.K. 100 blender, and the mixture is blended for five minutes. The magnesium oxide (heavy, D.C.), calcium carbonate (gran. D.C./A.), dicalcium phosphate (dihyd., unmilled), copper gluconate, chromium trituration (10%), molybdenum trituration (10%), selenium trituration (10%), manganese gluconate (FCC), and zinc gluconate (gran.) are passed through a SWECO separator equipped with a 6-mesh screen into the P.K. 100 blender.

Potassium chloride, microcrystalline cellulose (silicified), and cellulose gum (modified) are passed through a SWECO separator equipped with a 20 mesh screen into the P.K. 100 blender. The mixture is blended for 20 minutes. Magnesium stearate (vegetable) is passed through a SWECO separator equipped with a 20 mesh screen directly into the P.K. 100 blender. The mixture is blended for an additional 5 minutes.

The resulting mixture is discharged into totes or supersacks, compressed, and punched by means known to those of ordinary skill in the art to form the tablets.

Tablet 3

Phytonadione (1%, S.D.), is passed through a SWECO separator equipped with a 20 mesh screen into a polylined container, and transferred to a 55-gallon stainless steel drum.

Vanadyl sulfate is passed though a 30-mesh testing sieve into its matching bottom pan. Any lumps or residue is forced through the screen. The vanadium is then transferred, without rescreening, directly on top of the phytonadione in the stainless steel drum.

Cellulose gum (modified NF) is passed through a SWECO separator equipped with a 20-mesh screen into a polylined container, and is transferred to the stainless steel drum.

The mixture in the stainless steel drum is blended on a drum tumbler for 10 minutes.

Vitamin E d-α-tocosuccinate is passed through a SWECO separator equipped with a 6-mesh screen directly into a P.K. 100 blender. Silicon dioxide (NF fine powder) is passed through a SWECO separator equipped with a 20 mesh screen directly into the P.K. 100 blender. The mixture is blended for ten minutes.

The concentrate (Double X Gold Standard concentrate) is passed through a SWECO separator equipped with a 6-mesh screen into the P.K. 100 blender. The mixture is blended for five minutes. Calcium carbonate (gran., D.C./A.), the phytonadione (1%, S.D.) (above), and magnesium oxide (heavy, D.C.) is passed through a SWECO separator equipped with a 6 mesh screen into the P.K. 100 blender. Microcrystalline cellulose (silicified) is passed through a SWECO separator equipped with a 20 mesh screen into the P.K. 100 blender, and the mixture is blended for 20 minutes.

Magnesium stearate (vegetable) is passed through a SWECO separator equipped with a 20-mesh screen into the P.K. 100 blender, and the mixture is blended for 20 minutes.

The resulting mixture is discharged into totes or polylined drums, and is compressed and punched, by means known to those of ordinary skill in the art, to form the tablets.

It will be apparent to those skilled in the art that various modifications and variations can be made in the compositions and methods of the present invention without departing from the spirit or scope of the invention. Thus, it is intended that the present description cover the modifications and variations of this invention provided that they come within the scope of the appended claims and their equivalents.

What is claimed is:

1. A dietary supplement composition comprising sulphoraphane, naringen, hesperidin, narirutin, quercetin, β-carotene, lutein, lycopene, and isoflavones.

2. A dietary supplement composition according to claim 1, wherein said phytochemicals are obtained from the following combination of plant concentrates: brassica concentrate, citrus bioflavonoid concentrates, quercetin, natural β-carotene concentrate, lutein, lycopene, soy isoflavone concentrate, spirulina concentrate, acerola cherry concentrate, alfalfa concentrate, and alfalfa/watercress/parsley concentrate.

3. A dietary supplement composition according to claim 1, wherein said sulphoraphane is obtained from brassica concentrate.

4. A dietary supplement composition according to claim 1, wherein said naringen, hesperidin, and narirutin are obtained from citrus bioflavonoid concentrates.

5. A dietary supplement composition according to claim 1, further comprising vitamins and minerals.

6. A dietary supplement composition according to claim 5, wherein said vitamins are chosen from vitamin A, vitamin C, vitamin D, vitamin E, vitamin K, thiamin, riboflavin, niacin, vitamin $B_6$, vitamin $B_{12}$, folic acid, biotin, and pantothenic acid.

7. A dietary supplement composition according to claim 5, wherein said minerals are chosen from calcium, magnesium, iodine, potassium, copper, zinc, phosphorus, manganese, chromium, selenium, molybdenum, vanadium, and boron.

8. A method for correcting a dietary inadequacy of phytochemicals comprising administering a dietary supplement to a subject known to have an inadequate phytochemical intake, wherein said dietary supplement comprises the following phytochemicals: sulphoraphane, naringen, hesperidin, narirutin, quercetin, β-carotene, lutein, lycopene, and isoflavones.

9. A method for correcting a dietary inadequacy of phytochemicals according to claim 8, wherein the deficiency is diet-induced.

10. A method for correcting a dietary inadequacy of phytochemicals according to claim 8, wherein the supplement additionally comprises vitamins and minerals.

11. A method for correcting a dietary inadequacy of phytochemicals according to claim 10, wherein said vitamins are chosen from vitamin A, vitamin C, vitamin D, vitamin E, vitamin K, thiamin, riboflavin, niacin, vitamin $B_6$, vitamin $B_{12}$, folic acid, biotin, and pantothenic acid.

12. A method for correcting a dietary inadequacy of phytochemicals according to claim 10, wherein said minerals are chosen from calcium, magnesium, iodine, potassium, copper, zinc, phosphorus, manganese, chromium, selenium, molybdenum, vanadium, and boron.

13. A method for correcting a dietary inadequacy of phytochemicals according to claim 8, wherein said phytochemicals are obtained from plant sources comprising plant materials chosen from alfalfa, watercress, parsley, Fava d'Anta, tomato, broccoli, horseradish, grapefruit, mandarin, lemon, Spirulina, algae, carrot, palm, marigold, tomato, and acerola.

14. A method for correcting a dietary inadequacy of phytochemicals according to claim 8, wherein said sulphoraphane is obtained from brassica concentrate.

15. A method for correcting a dietary inadequacy of phytochemicals according to claim 8, wherein said naringen, hesperidin, and narirutin are obtained from citrus bioflavonoid concentrates.

16. A method for correcting a dietary inadequacy of phytochemicals according to claim 8, wherein said dietary supplement is administered to said subject in the form of three tablets administered twice a day.

17. A method for increasing plasma levels of vitamin E, vitamin $B_{12}$, $\beta$-carotene, and folate comprising administering a dietary supplement composition according to claim 5 to a subject in need thereof.

18. A method for increasing plasma levels of vitamin E, vitamin $B_{12}$, $\beta$-carotene, and folate comprising administering a dietary supplement composition according to claim 6 to a subject in need thereof.

* * * * *